US00PP14219P29

(12) United States Plant Patent
Bradford

(10) Patent No.: US PP14,219 P2
(45) Date of Patent: Oct. 7, 2003

(54) PLUM TREE NAMED 'PLUMSWEETONE'

(50) Latin Name: *Prunus salicina*
Varietal Denomination: 'Plumsweetone'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/300,252

(22) Filed: Nov. 21, 2002

(51) Int. Cl.[7] ..... A01H 5/00
(52) U.S. Cl. ..... Plt./184
(58) Field of Search ..... Plt./184

*Primary Examiner*—Bruce R. Campell
*Assistant Examiner*—Susan B. McCormick

(57) ABSTRACT

The present invention relates to a plum tree, *Prunus salicina,* and more particularly to a new and distinct variety broadly characterized by a medium size, vigorous, hardy, heavy blooming, pollen abundant, self-unfruitful, and usually productive tree. The present variety requires cross pollinization from another plum that blooms during the mid season, such as Fortune (unpatented) The fruit matures under the ecological conditions described during the last week in June, with first picking on Jun. 29, 2002. The fruit is uniformly medium in size, a two-tone purple over yellow in skin color, clingstone in type, purely yellow with no red bleeding in flesh color, very firm and crisp in texture, very good in flavor, and holds well in cold storage for more than thirty days. The variety was developed as an open pollinated seedling of 'Ambra' (unpatented).

1 Drawing Sheet

Botanical classification: *Prunus salicina.*
Variety denomination: 'Plumsweetone'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of plum tree, which has been denominated varietally as 'Plumsweetone'. During the spring of 1997, I gathered fruit from several different 'Ambra' (unpatented) plum trees located in my experimental orchard at Bradford Farms near Le Grand, Calif. in Merced County (San Joaquin Valley). The seeds from that fruit were removed, cracked, stratified, germinated, and grown as seedlings on their own root in my greenhouse. Upon reaching dormancy that year, they were transplanted to a cultivated area of the experimental orchard described above and were labeled "Ambra (OP)". During the fruit evaluation season of 2000, I selected several plum trees that showed excellent characteristics. The present variety was selected as a single tree among the group described above. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Ambra' (unpatented), by producing an abundance of blossoms and pollen, by being self-unfruitful, and by producing plums that are sweet, firm, and somewhat oblate in shape, but is very distinguished therefrom and an improvement thereon by blooming about one week later and by producing plums that are a purple over yellow two-tone rather than black in skin color, that have a much smoother skin finish, and that mature about twelve days later.

The present variety is most similar to Blackamber (unpatented) plum by being self-unfruitful, by blooming in the mid season and by producing plums that are somewhat oblate in shape, medium in size, and mature in the mid season, but is distinguished therefrom and an improvement thereon by blooming heavier and by producing plums that are a purple over yellow two-tone in skin color rather than black, that are much sweeter in flavor, and that mature about one week earlier.

SUMMARY OF VARIETY

The present plum variety is characterized by a medium size, vigorous, hardy, and usually productive tree. Being self-unfruitful, the present variety requires cross pollinization from another plum that blooms during the mid season, such as Fortune (unpatented). The present variety's abundance of blossoms and pollen entices strong bee activity to facilitate pollination. The fruit matures under the ecological conditions described during the last week in June, with first picking on Jun. 29, 2002. The fruit is uniformly medium in size, a two-tone purple over yellow in skin color, clingstone in type, purely yellow with no red bleeding in flesh color, very firm and crisp in texture, very good in flavor, and holds well in cold storage for more than thirty days.

DRAWING

The accompanying photograph exhibits four whole fruits positioned to display the characteristics of the skin color and form, one fruit divided transversely to the suture plane to reveal the flesh and stone, and typical leaves.

DETAILED BOTANICAL DESCRIPTION

Referring now more specifically to the pomological characteristics of this new and distinct variety of plum tree, the following has been observed under the ecological conditions prevailing near Le Grand, Merced County (San Joaquin Valley), Calif., and was developed at the state of shipping ripe on Jul. 2, 2002, on the original tree during its sixth growing season. All major color code designations are by reference to the Inter-Society Color Council, National Bureau of Standards. Common color names are also used occasionally.

Tree

Size: Medium, reaching and maintaining a height of 10' [3.0 m.] and a spread of 7' [2.1 m.] after five growing seasons utilizing typical dormant pruning.

Vigor: Vigorous, responding typically to irrigation and fertilization. The variety grows about 4' [1.2 m.] of surplus top-growth during the spring and summer. The plant should be grown on a standard commercial rootstock for production purposes.

Growth: Upright and open.

Form: Vase formed.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Very productive, thinning usually necessary.

Fertility: Self-unfruitful, requiring cross pollination by a suitable mid seasonal blooming plum, such as 'Santa Rosa' (unpatented).

Bearing: Usually consistent, but some uncertainty exists if inclement weather is encountered during the blooming period.

Trunk:

*Size.*—Slender, reaching a maximum diameter of 2⅜" [60 mm.] after the fifth growing season.

*Texture.*—Shaggy.

*Bark color.*—Dark grayish brown [62. d.gy.Br] with Light brown [57. l.Br] crevices streaked throughout.

*Lenticels.*—Approximate Number Per Square Inch: 18. Color: Brownish orange [54. brO]. Typical Size: ⅛" to ⅜" [3.2–9.5 mm.].

Branches:

*Size.*—Diameter of limb is 1¼" [32 mm.] measured 12" above the first fork, typical of *Prunus salicina,* and dependent upon cultural practices and climatic conditions.

*Texture.*—Smooth on first and second year wood, increasing roughness with age.

*Color.*—1st Year Wood Topside: Deep yellowish brown [75. deep yBr] where exposed to sunlight. 1st Year Wood Underside: Strong yellow green [117. s.YG]. Older Wood: Deep yellowish brown [75. deep yBr].

*Lenticels.*—Approximate Number Per Square Inch: 48. Color: Light orange yellow [70. l.OY]. Typical size: 1/32" to ⅛" [0.8–3.2 mm.].

Leaves:

*Size.*—Large. Average Length: 3¾" [95 mm.]. Average width: 2⅛" [54 mm.].

*Arrangement.*—Alternate.

*Thickness.*—Medium.

*Form.*—Oval to elliptical.

*Apex.*—Acute to somewhat acuminate.

*Base.*—Acute to rounded.

*Surface.*—Smooth.

*Color.*—Dorsal Surface: Dark yellowish green [137. d.yG]. Ventral Surface: Moderate yellowish green [136. m.yG].

*Margin.*—Finely serrate.

*Venation.*—Pinnately net veined.

*Petiole.*—Average length: ½" [12.7 mm.]. Average Thickness: 1/16" [1.6 mm.]. Color: Light yellowish green [135. l.yG] with two Grayish red [19. gy.R] streaks on some.

*Stipules.*—Number: 2 per leaf, up to 6 per growing tip. Average Length: 7/16" [11.1 mm.]. Color: Light yellowish green [135. l.yG] when growing.

*Glands.*—Number: Usually 1 or 2. Position: Alternate, positioned at the intersection of the petiole and base of blade. Size: Small. Form: Globose. Color: Grayish red [19. gy.R].

*Leaf buds.*—Conic.

Flower buds:

*Hardiness.*—Hardy, with respect to central California winters.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Pubescent.

*Color.*—White [263. White].

Flowers: Perfect, Complete, perigynous, usually a single pistil, typically twenty-eight or more stamens, five sepals and petal locations alternately positioned.

*Average flower diameter.*—13/16" [20.6 mm.].

*Number of petals.*—Five, no double blossoms observed.

*Petal shape.*—Oval.

*Petal margin.*—Slightly wavy.

*Average petal diameter.*—5/16" [7.9 mm.].

*Average petal length.*—⅜" [9.5 mm.].

*Petal apex.*—Rounded.

*Petal base.*—Rounded to somewhat acute.

*Petal color.*—White [263. White].

*Anther color.*—Brilliant yellow [83. brill.Y].

*Stigma color.*—Light yellow green [119. l.YG].

*Sepal color.*—Brilliant yellow green [116. brill.YG] with some Moderate purplish red [258. m.pR] tinging along the margins.

*Sepal length.*—5/32" [4 mm.].

*Sepal width.*—⅛" [3 mm.].

*Average pistil length.*—⅜" [9.5 mm.].

*Average stamen length.*—¼" [6.4 mm.].

*Fragrance.*—Moderate.

*Pollen production.*—Abundant.

*Blooming period.*—Medium compared with other varieties, approximately with 'Santa Rosa' (unpatented).

*Onset of bloom.*—One percent on Feb. 23, 2002.

*Date of full bloom.*—Mar. 5, 2002.

*Duration of bloom.*—One to two weeks, dependent on ambient temperature.

*Number per cluster.*—Average 5, up to 9 observed.

FRUIT

Maturity when described: Shipping ripe, Jul. 2, 2002.

Date of first picking: Jun. 29, 2002.

Date of last picking: Jul. 12, 2002.

Size: Uniform, medium.

*Average diameter axially.*—2 3/16" [55.6 mm.].

*Average diameter across suture plane.*—2 9/16" [65.1 mm.].

*Typical weight.*—4.5 ounces [128 grams].

Form: Uniform, mostly symmetrical, somewhat oblate, compressed axially.
*Longitudinal section form.*—Elliptical.
*Transverse section through diameter.*—Circular.
Suture: A distinct shallow groove extending from the base to the apex, but not beyond.
Ventral surface: Rounded, slightly lipped toward the base.
Lips: Equal.
Cavity: Flaring, circular to slightly elongated in the suture plane, suture showing on one side.
*Depth.*—7/16" [11.1 mm.].
*Breadth.*—1 1/16" [27.0 mm.].
Base: Truncate, but slightly cuneate when viewed along the suture.
Apex: Rounded, with a slight rounded hump at the end of the suture.
Pistil point: An inconspicuous dot at the top of the rounded hump.
Stem: Medium.
*Average length.*—½" [12.7 mm.].
*Average width.*—⅛" [3.2 mm.].
Skin:
*Thickness.*—Medium.
*Surface.*—Smooth.
*Tenacity.*—Tenacious to flesh.
*Astringency.*—Moderate.
*Tendency to crack.*—None observed.
*Color.*—Very dark purplish red [260. v.d.pR] smoothly blending to Dark red [16. d.R] usually with several Brilliant yellow [83. brill.Y] areas creating a two tone effect, Light orange yellow [70. l.0Y] freckling throughtout.
*Bloom.*—Abundant.
Flesh:
*Color.*—Light yellow [86. l.Y] toward the stone blending to Light orange yellow [70. l.OY] toward the skin with no streaking or bleeding.
*Surface of pit cavity.*—Covered with short Moderate yellow [87. m.Y] fibers breaking away from the stone when twisted.
*Amygdalin.*—Moderate.
*Juice.*—Very abundant, rich.
*Texture.*—Very firm, crisp.
*Fibers.*—Abundant, fine.
*Ripens.*—Slightly earlier toward the apex.
*Flavor.*—A tasty blend of acid and sugar, typically 19 brix.
*Aroma.*—Slight.
*Eating quality.*—Very good.

STONE

Type: Clingstone.
Form: Oval.
Hilum: Narrow, oblong.
Base: Rounded with a unique half-moon notch surrounding the hilum.
Apex: Rounded to slightly wedge shaped, no tip.
Sides: Equal.
Surface: Rough.
Ridges: One sharp dorsal fin extending from the hilum to the apex.
External color of stone: Dark orange yellow [72. d.OY].
Pit wall when cracked: Light yellowish brown [76. l.yBr].
Cavity surface color: Moderate yellowish brown [77. m.yBr].
Average pit wall thickness: 1/16" [1.6 mm.].
Average width: 13/16" [20.6 mm.].
Average length: 15/16" [23.8 mm.].
Average breadth: ⅜" [9.5 mm.].
Tendency to split: Very slight.
Kernel:
*Form.*—Oval.
*Pellicle color.*—Grayish yellow [90. gy.Y].
*Skin color.*—Light yellow [86. l.Y].
*Taste.*—Bitter.
*Viable.*—Yes.
*Average width.*—½" [12.7 mm.].
*Average length.*—⅝" [15.9 mm.].
*Amygdalin.*—Abundant.

USE

Market: Fresh market and long distance shipping.
Keepinq quality: Excellent. Fruit quality observed to remain in good condition in after 30 days in standard cold room at 36° Fahrenheit [2° Celsius].
Shipping quality: Excellent.
Resistance to insects: No unusual susceptibilities noted.
Resistance to diseases: No unusual susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is most similar to Blackamber (unpatented) plum by being self-unfruitful, by blooming in the mid season and by producing plums that are somewhat oblate in shape, medium in size, and mature in the mid season, but is distinguished therefrom and an improvement thereon by blooming heavier, by producing more pollen, and by producing plums that are a purple over yellow two-tone in skin color rather than black, that are much sweeter in flavor, and that mature about one week earlier.

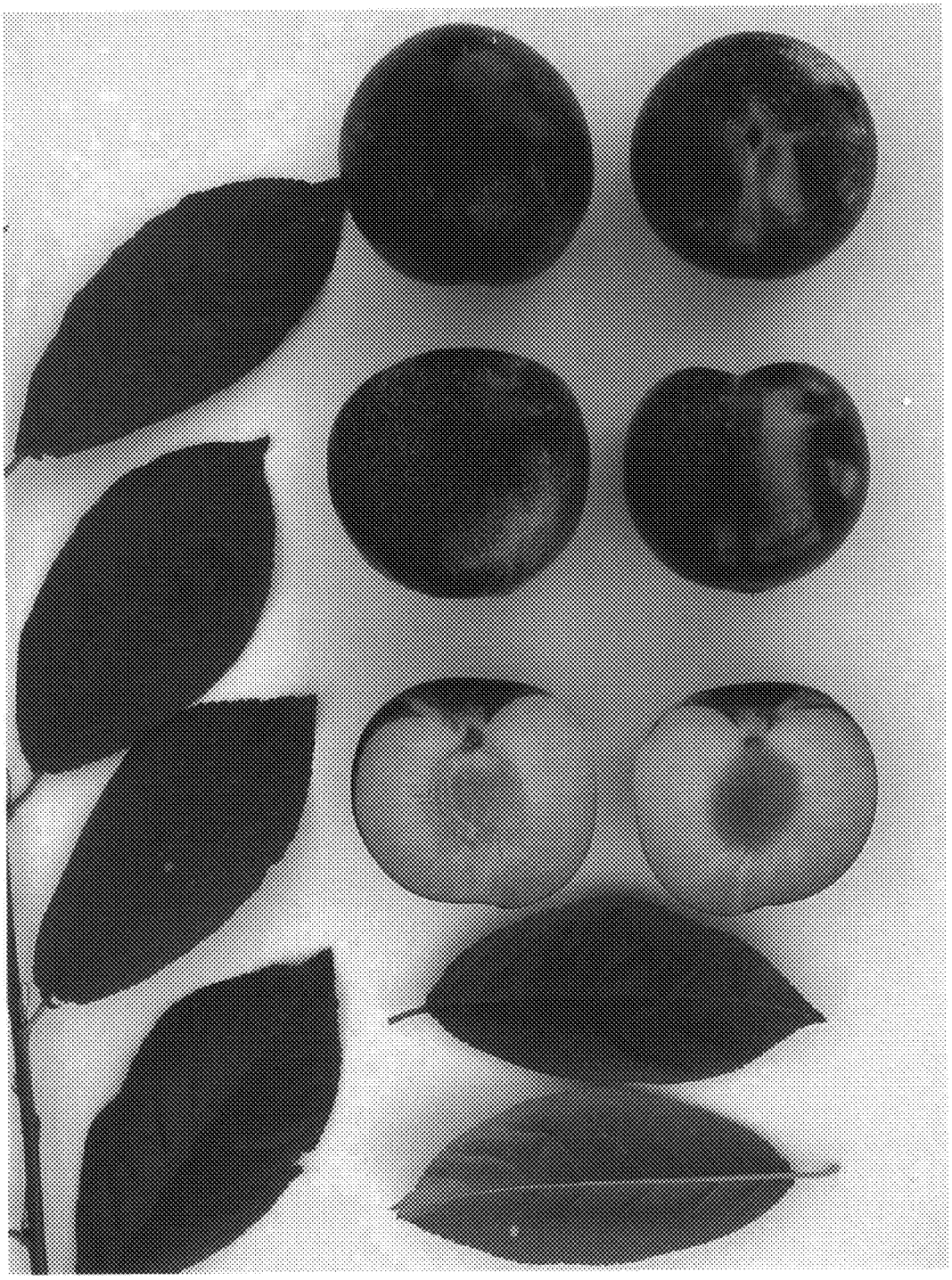

* * * * *